(12) United States Patent
Zhang

(10) Patent No.: US 12,723,973 B2
(45) Date of Patent: Sep. 1, 2026

(54) GAS SENSOR

(71) Applicant: AAC ACOUSTIC TECHNOLOGIES (SHENZHEN) CO., LTD., Shenzhen (CN)

(72) Inventor: Jinyu Zhang, Shenzhen (CN)

(73) Assignee: AAC ACOUSTIC TECHNOLOGIES (SHENZHEN) CO., LTD., Shenzhen (CN)

( * ) Notice: Subject to any disclaimer, the term of this patent is extended or adjusted under 35 U.S.C. 154(b) by 285 days.

(21) Appl. No.: 18/399,718

(22) Filed: Dec. 29, 2023

(65) Prior Publication Data

US 2024/0337588 A1 Oct. 10, 2024

Related U.S. Application Data

(63) Continuation of application No. PCT/CN2023/086222, filed on Apr. 4, 2023.

(51) Int. Cl.
*G01N 21/17* (2006.01)
*G01N 33/00* (2006.01)

(52) U.S. Cl.
CPC ..... *G01N 21/1702* (2013.01); *G01N 33/0027* (2013.01); *G01N 2021/1704* (2013.01)

(58) Field of Classification Search
CPC ........... G01N 21/1702; G01N 33/0027; G01N 2021/1704
USPC ........................................................ 73/24.02
See application file for complete search history.

(56) References Cited

U.S. PATENT DOCUMENTS

| | | | | |
|---|---|---|---|---|
| 5,933,245 | A * | 8/1999 | Wood | G01N 21/1702 356/440 |
| 8,695,402 | B2 * | 4/2014 | Thorson | G01N 21/1702 73/24.02 |
| 2015/0101395 | A1 * | 4/2015 | Dehe | G01N 29/30 73/24.02 |
| 2017/0350810 | A1 * | 12/2017 | Tumpold | G01N 21/1702 |
| 2017/0350868 | A1 * | 12/2017 | Tumpold | G01N 29/34 |
| 2018/0120266 | A1 * | 5/2018 | Tumpold | G01N 29/222 |
| 2022/0283123 | A1 * | 9/2022 | Bürgi | G01N 21/1702 |

* cited by examiner

*Primary Examiner* — Nathaniel T Woodward
(74) *Attorney, Agent, or Firm* — Wiersch Law Group

(57) ABSTRACT

The present disclosure provides a shell with a receiving cavity, an infrared transmitter and an acoustic sensor accommodated in the receiving cavity, and a flexible film connected with the side wall, the shell includes a cover, a substrate, and a side wall, the flexible film divides the receiving cavity into a first cavity and a second cavity, the infrared transmitter is located in the first cavity, the acoustic sensor is located in the second cavity, the shell comprises a vent hole communicating with an outside and the first cavity, the flexible film, the first cavity and the second cavity form a resonant system, an intrinsic frequency of the resonant system is the same as a modulation frequency of the infrared transmitter. Compared with the related art, the gas sensor disclosed by the present disclosure could improve the sensitivity of the product.

7 Claims, 3 Drawing Sheets

GAS SENSOR

FIELD OF THE PRESENT DISCLOSURE

The present disclosure relates to the technical field of sensors, and in particular relates to a gas sensor.

DESCRIPTION OF RELATED ART

A gas sensor is a converter that converts a certain gas volume fraction into a corresponding electric signal. Existing gas sensors usually include a housing, a damping net, a substrate, an infrared transmitter, and an acoustic sensor, the external gas passes through the damping net through diffusion and is balanced with the internal gas concentration. When the sensor is working, the infrared transmitter emits infrared light of a specific wavelength at a certain sound frequency (e.g., 30 Hz). This wavelength of the infrared light is strongly absorbed by the gas to be measured and converted into heat. An alternating pressure signal is generated in the internal chamber, which is received by the acoustic sensor and converted into an electric signal. The higher the concentration of the gas to be measured in the gas, the stronger the low frequency signal is. From the signal strength output by the microphone, the concentration of the gas to be measured can be calculated.

The infrared transmitter and the acoustic sensor in the related art are located in the same cavity. The modulated infrared signal produces electrical interference to the acoustic sensor, leading to measurement errors. The low strength of the electrical signal excited by the infrared signal will lead to a lack of sensitivity of the gas sensor. In addition, the external sound signal will form a strong noise interference to the gas sensor, resulting in inaccurate detection results of the gas sensor.

Therefore, it is necessary to provide a gas sensor to solve the above problems.

SUMMARY OF THE PRESENT DISCLOSURE

The present disclosure is to provide a gas sensor, which can solve the technical problem that the gas sensor in the related art has a lack of sensitivity.

For achieving the object mentioned above, the disclosure provides a gas sensor, including a shell with a receiving cavity, an infrared transmitter and an acoustic sensor accommodated in the receiving cavity, and a flexible film connected with the side wall, the shell includes a cover, a substrate spaced apart from the cover, and a side wall located between the cover and the substrate, the flexible film divides the receiving cavity into a first cavity and a second cavity, the first cavity is formed by the joint enclosure of the flexible film, the side wall and the cover, the second cavity is formed by the joint enclosure of the flexible film, the side wall and the substrate, the infrared transmitter is located in the first cavity, the acoustic sensor is located in the second cavity, the shell comprises a vent hole communicating with an outside and the first cavity, the flexible film, the first cavity and the second cavity form a resonant system, an intrinsic frequency of the resonant system is the same as a modulation frequency of the infrared transmitter.

As an improvement of the above, the side wall comprises a first side wall connected with the cover and a second side wall connected with the substrate, the flexible film is sandwiched with the first side wall and the second side wall.

As an improvement of the above, the infrared transmitter is fixed with the cover.

As an improvement of the above, the acoustic sensor is fixed with the substrate.

As an improvement of the above, a volume of the first cavity is larger than that of the second cavity.

As an improvement of the above, the vent hole is provided in the cover.

As an improvement of the above, the flexible film comprises an upper surface located in the first cavity, and the upper surface of the flexible film includes an aluminum reflective layer or a silver reflective layer.

a gas sensor, including:

a shell with a receiving cavity, comprising a cover, a substrate spaced apart from the cover, and a side wall located between the cover and the substrate, the cover, the substrate, and the side wall jointly enclosing to form the receiving cavity, and an infrared transmitter, an acoustic sensor, a partition plate and a flexible film accommodated in the receiving cavity, wherein the partition plate is connected with the substrate and the side wall, the flexible film is located between the cover and the side wall, the flexible film covers the side wall and the partition plate, the partition plate and the flexible film jointly divide the receiving cavity into a first cavity and a second cavity, the first cavity is a sealed cavity formed by the joint enclosure of the flexible film, the partition plate, the side wall and the substrate, the acoustic sensor is located in the first cavity, the infrared transmitter is located in the second cavity, the shell comprises a vent hole communicating with the outside and the second cavity, the flexible film, the first cavity and the second cavity form a resonant system, an intrinsic frequency of the resonant system is the same as a modulation frequency of the infrared transmitter.

As an improvement of the above, the cover comprises a top plate, a connecting portion bending and extending from the top plate to the side wall, and a fixing portion bending and extending from the connecting portion to the outside, the fixing portion is fixed with an upper surface of the side wall.

As an improvement of the above, the fixing portion is smaller than the upper surface of the side wall, one end of the flexible film is connected to the upper surface of the side wall and the other end of the flexible film is connected to the partition plate, the flexible film is located at an internal side of the fixing portion.

As an improvement of the above, the gas sensor further comprises a weight connected with the flexible film.

As an improvement of the above, the weight is located in the first cavity.

As an improvement of the above, the side wall comprises two first side walls located on long-axis sides and two second side walls located on short-axis sides, the partition plate is connected with the two first side walls opposite to each other.

As an improvement of the above, the partition plate and the side wall are configured as an integrated structure.

As an improvement of the above, the acoustic sensor and the infrared transmitter are fixed with the substrate.

BRIEF DESCRIPTION OF THE DRAWINGS

Many aspects of the exemplary embodiments can be better understood with reference to the following drawings. The components in the drawing are not necessarily drawn to scale, the emphasis instead being placed upon clearly illustrating the principles of the present disclosure.

DETAILED DESCRIPTION OF THE EXEMPLARY EMBODIMENTS

The present disclosure will hereinafter be described in detail with reference to several exemplary embodiments. To make the technical problems to be solved, technical solutions and beneficial effects of the present disclosure more apparent, the present disclosure is described in further detail together with the figures and the embodiments. It should be understood the specific embodiments described hereby are only to explain the disclosure, not intended to limit the disclosure.

Figure 1:
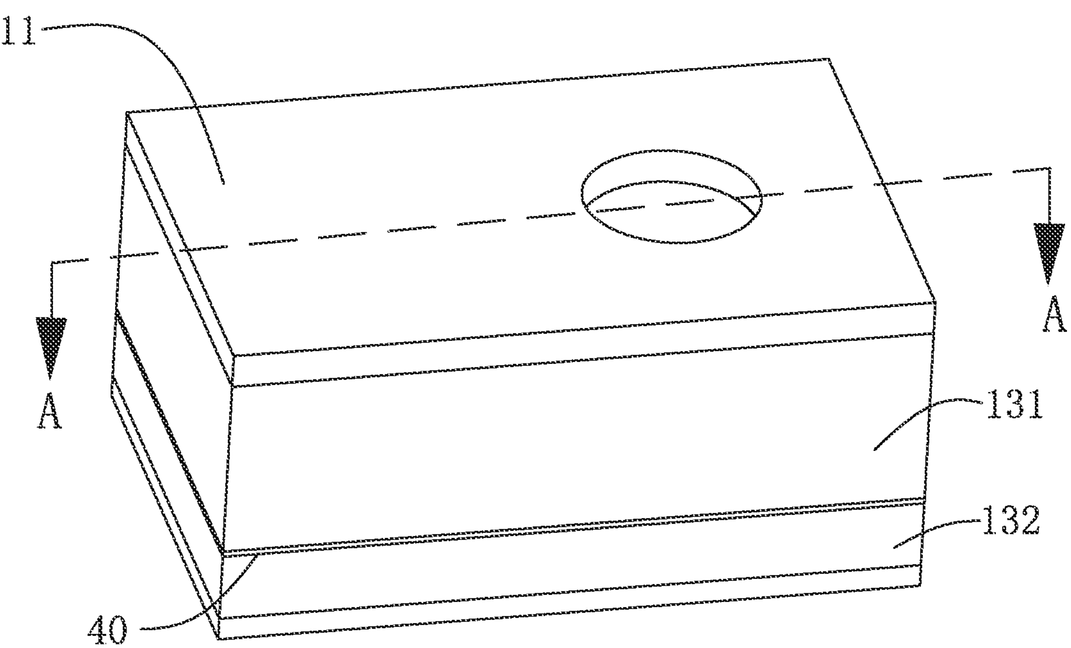
FIG. 1 is an isometric view of a gas sensor in accordance with an exemplary embodiment of the present disclosure.
Figure 2:
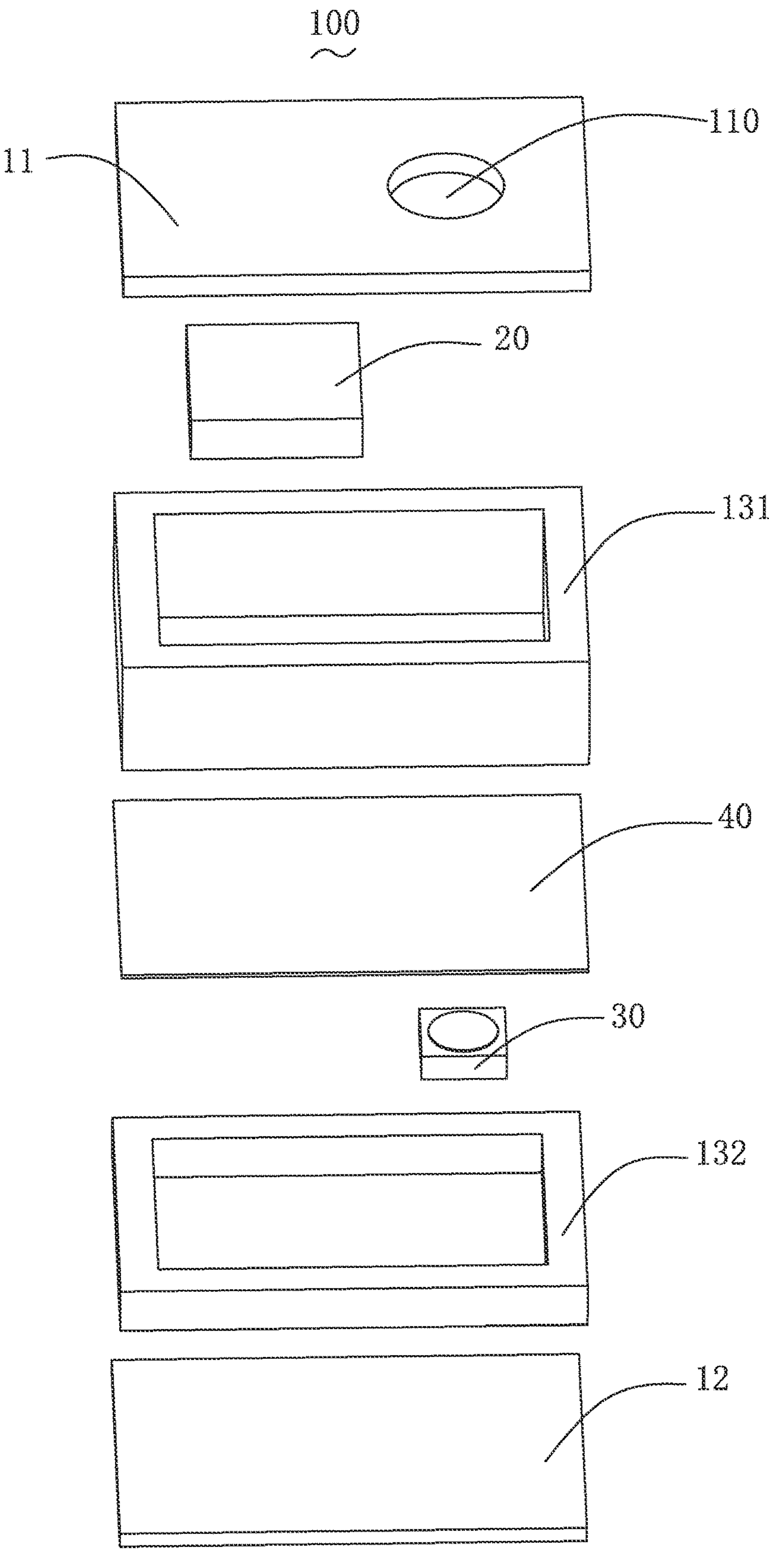
FIG. 2 is an exploded view of the gas sensor in FIG. 1.
Figure 3:
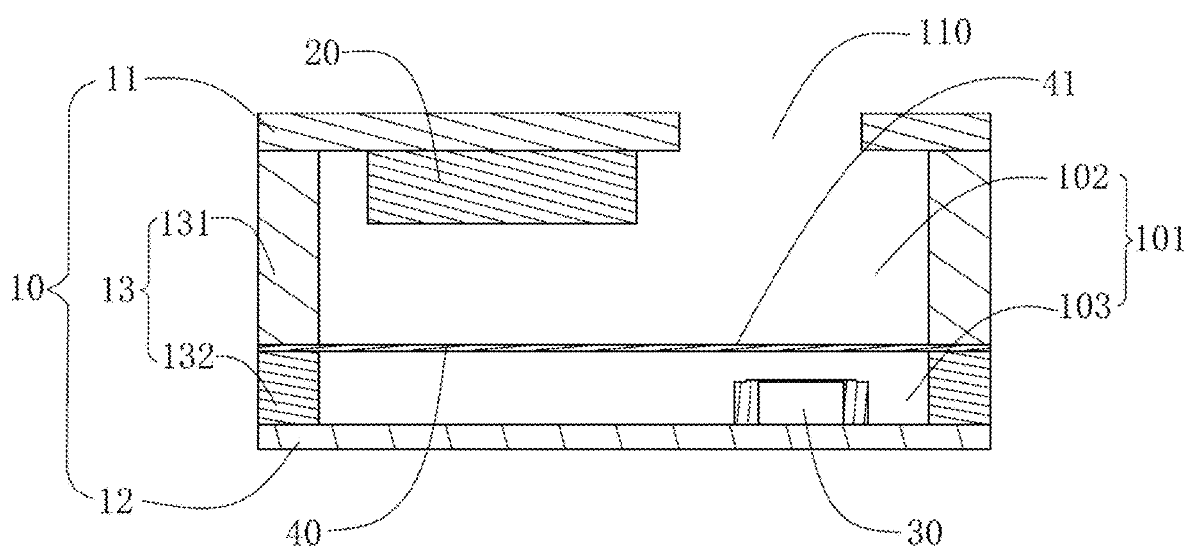
FIG. 3 is a cross-sectional view of the gas sensor taken along line A-A in FIG. 1.

Please refer to FIGS. 1-3, a gas sensor 100 includes a shell 10 with a receiving cavity 101, and an acoustic sensor 30 and an infrared transmitter 20 located in the receiving cavity 101. The shell 10 includes a cover 11, a substrate 12 spaced apart from the cover 11, and a side wall 13 located between the cover 11 and the substrate 12. The infrared transmitter 20 emits light into the receiving cavity 101, the emitted light may be infrared light, in particular, pulsed light, such as pulsed infrared light. The acoustic sensor 30 may include a microphone, in particular a MEMS microphone which detects an acoustic signal caused by the emitted light according the photoacoustic principle.

In the present embodiment, the gas sensor 100 further includes a flexible film 40 connected with the side wall 13 and located in the receiving cavity 101, the flexible film 40 divides the receiving cavity 101 into a first cavity 102 and a second cavity 103. The first cavity 102 is formed by the joint enclosure of the flexible film 40, the side wall 13 and the cover 11, the second cavity 103 is formed by the joint enclosure of the flexible film 40, the side wall 13 and the substrate 12, the infrared transmitter 20 is located in the first cavity 102, the acoustic sensor 30 is located in the second cavity 103. The flexible film 40, the first cavity 102 and the second cavity 103 form a resonant system, an intrinsic frequency of the resonant system is the same as a modulation frequency of the infrared transmitter 20. The shell 10 includes a vent hole 110 communicating with the receiving cavity 101, in the present embodiment, the vent hole 110 is communicating with the first cavity 102.

The side wall 13 includes a first side wall 131 connected with the cover 11 and a second side wall 132 connected with the substrate 12, the flexible film 40 is sandwiched between the first side wall 131 and the second side wall 132, that is, the flexible film 40, the side wall 13 and the cover 11 jointly form the first cavity 102, the flexible film 40, the side wall 13 and the substrate 12 jointly form the second cavity 103. The split design of the side wall 13 could facilitate the fixed installation of the flexible film 40. In addition, a volume of the first cavity 102 is larger than that of the second cavity 103. In other embodiments, the side wall can also be equipped with grooves to accommodate and fix the flexible film, as long as the flexible film can be fixed.

The outside gas enters into the first cavity 102 through the vent hole 110, the infrared transmitter 20 emits infrared light of a specific wavelength at a certain frequency (e.g., 30 Hz), this wavelength of the infrared light is strongly absorbed by the gas to be measured and converted into heat, an alternating pressure signal is generated in the first cavity 102, the flexible film 40 is driven to resonate, thus creating a strong acoustic resonance signal in the second cavity 103, which is thereby converted into an electrical signal. According to the signal strength output by the acoustic sensor 30, the concentration of the gas to be measured can be calculated.

In the present embodiment, as the infrared emitter 20 and the acoustic sensor 30 are arranged in different cavities, the generation of interference signals can be avoided. In addition, the modulation frequency of infrared transmitter 20 is the same as the resonance frequency of flexible film 40, the flexible film 40 is in resonance, thereby forming the acoustic resonance, which can enhance the sound signal by 20 dB and significantly improve the sensitivity of the product. The modulation frequency of the infrared transmitter 20 is in a range of 40 Hz-60 Hz which is much lower than a frequency of ambient noise, ambient noise is isolated by the flexible film 40, which will not interfere with the acoustic sensor 30, the acoustic sensor 30 is located in the sealed second cavity 103, which prevents particles from entering the second cavity 103 and causing the acoustic sensor 30 to fail.

Preferably, the flexible film 40 includes an upper surface 41 located in the first cavity 102, the upper surface 41 is opposite to the cover 11. The upper surface 41 of the flexible film 40 includes an aluminum reflective layer or a silver reflective layer, which could improve the efficiency of infrared signal utilization while reducing the light interference to acoustic sensor 30.

In addition, the infrared transmitter 20 is fixed to the cover 11, and the acoustic sensor 30 is fixed to the substrate 12, the vent hole 110 is provided in the cover 11.

It is to be understood, however, that even though numerous characteristics and advantages of the present exemplary embodiments have been set forth in the foregoing description, together with details of the structures and functions of the embodiments, the disclosure is illustrative only, and changes may be made in detail, especially in matters of shape, size, and arrangement of parts within the principles of the disclosure to the full extent indicated by the broad general meaning of the terms where the appended claims are expressed.

What is claimed is:

1. A gas sensor, including:

a shell with a receiving cavity, the shell comprising a cover, a substrate spaced apart from the cover, and a side wall located between the cover and the substrate;

an infrared transmitter and an acoustic sensor accommodated in the receiving cavity, and a flexible film connected with the side wall, wherein the flexible film divides the receiving cavity into a first cavity and a second cavity;

the first cavity is formed by the joint enclosure of the flexible film, the side wall and the cover;

the second cavity is formed by the joint enclosure of the flexible film, the side wall and the substrate;

the infrared transmitter is located in the first cavity;

the acoustic sensor is located in the second cavity;

the shell comprises a vent hole communicating with an outside and the first cavity; and wherein the flexible film, the first cavity and the second cavity form a resonant system, an intrinsic frequency of the resonant system is the same as a modulation frequency of the infrared transmitter.

2. The gas sensor as described in claim 1, wherein the side wall comprises a first side wall connected with the cover and a second side wall connected with the substrate, the flexible film is sandwiched with the first side wall and the second side wall.

3. The gas sensor as described in claim 1, wherein the infrared transmitter is fixed with the cover.

4. The gas sensor as described in claim 1, wherein the acoustic sensor is fixed with the substrate.

5. The gas sensor as described in claim 1, wherein a volume of the first cavity is larger than that of the second cavity.

6. The gas sensor as described in claim 1, wherein the vent hole is provided in the cover.

7. The gas sensor as described in claim 1, wherein the flexible film comprises an upper surface located in the first cavity, and the upper surface of the flexible film includes an aluminum reflective layer or a silver reflective layer.

* * * * *